(12) United States Patent
Tsuru

(10) Patent No.: US 7,738,119 B2
(45) Date of Patent: Jun. 15, 2010

(54) OPTICAL INSPECTION SYSTEM FOR A WAFER

(75) Inventor: Kiyohiro Tsuru, Chiba (JP)

(73) Assignee: Seiko Instruments Inc., Chiba (JP)

( * ) Notice: Subject to any disclaimer, the term of this patent is extended or adjusted under 35 U.S.C. 154(b) by 94 days.

(21) Appl. No.: 12/015,849

(22) Filed: Jan. 17, 2008

(65) Prior Publication Data

US 2008/0316506 A1 Dec. 25, 2008

(30) Foreign Application Priority Data

Jan. 29, 2007 (JP) .............................. 2007-017602

(51) Int. Cl.
*G01B 11/28* (2006.01)
*G01N 21/00* (2006.01)
(52) U.S. Cl. .................. 356/630; 356/237.4; 356/237.5
(58) Field of Classification Search ....................... None
See application file for complete search history.

(56) References Cited

U.S. PATENT DOCUMENTS 7,375,829 B2 * 5/2008 Kang .......................... 356/630

FOREIGN PATENT DOCUMENTS

JP 2004-93338 A 3/2004

\* cited by examiner

*Primary Examiner*—Tarifur Chowdhury
*Assistant Examiner*—Gordon J Stock, Jr.
(74) *Attorney, Agent, or Firm*—Brinks Hofer Gilson & Lione

(57) ABSTRACT

Provided is an optical inspection system for a semiconductor wafer, by which a threshold value optimal for inspection can be determined and optical inspection of each chip can be performed based on the threshold value, by obtaining in advance a table indicating a relation between a film thickness of a thin film in specific positions in the wafer and a gradation value for each sample area in the chip, measuring the film thickness of the thin film in the specific positions of the wafer to be inspected before inspecting the chip, and comparing the measured film thickness with the gradation value in the table.

6 Claims, 3 Drawing Sheets

OPTICAL INSPECTION SYSTEM FOR A WAFER

This application claims priority under 35 U.S.C. §119 to Japanese Patent Application No. JP2007-017602 filed Jan. 29, 2007, the entire content of which is hereby incorporated by reference.

BACKGROUND OF THE INVENTION

1. Field of the Invention

The present invention relates to an optical inspection system for performing optical inspection of a wafer and a semiconductor substrate, and more particularly, to an optical inspection system for detecting defects on a wafer, which are generated in the manufacturing process of semiconductor integrated circuits.

2. Description of the Related Art

A method of comparing an inspection target image data with a reference image data to check the integrity of an inspection target based on any accidental difference between them is conventionally known as optical inspection method for detecting conformity of pattern formed on an inspection target (a semiconductor wafer) and defects such as foreign substances and scratches on the pattern.

For example, through image data input means for gray scale image data representing an appearance of the inspection target in gray scale, and statistical processing means for calculating, as statistical data, reference image data and dispersion data based on a plurality of gray scale image data representing appearances of a plurality of inspection targets in gray scale, the statistical data calculated by the statistical processing means, discriminant data for determining acceptability of the inspection target, which is set in advance, and the gray scale image data of the inspection target, which is an input from the image data input means, are used to check integrity of the inspection target for each pixel, thereby determining acceptability of the inspection target.

As a method for determining acceptability, there is a method of calculating dispersion data and an average value of reference image data based on gray scale image data of a plurality of acceptable inspection targets in the statistical processing means, and calculating the range of acceptability based on the dispersion data and the average value of the reference image data, thereby determining acceptability of the inspection target. Further, the range of acceptability is set to different values for each of a plurality of areas with different position coordinates of gray scale image data, thereby determining acceptability of the inspection target with different inspection accuracy for each of the plurality of areas with different position coordinates of the gray scale image data (see, for example, JP 2004-93338 A).

In the conventional art described above, the standard for acceptability can be set in advance with different accuracy for each of the plurality of areas with different position coordinates. However a semiconductor device is, in general, manufactured by forming various thin films such as a silicon oxide film, a silicon nitride film, and polysilicon film on a semiconductor wafer, thickness variation in each of the various thin films occurs between lots, in a lot, and even in a wafer depending on the capacity of production equipment, which leads to a problem that a gray scale image of each chip on a semiconductor wafer changes, and in the case where film thickness of various thin films deviates from the range of the film thickness variation estimated in advance, the chip is detected as a defective chip despite absence of foreign substances and defective patterns.

SUMMARY OF THE INVENTION

A relation between film thickness of a thin film at specific positions of a wafer and a gradation value for each sampling area in a chip of the wafer is obtained in advance as a table, the film thickness of the thin film in the specific positions of the wafer to be inspected is measured at a time before inspecting the chip, such as at the time of wafer alignment, and the measured film thickness is compared with the gradation value in the table, thereby determining a threshold value optimal for the inspection and performing optical inspection of each chip based on the threshold value.

In such a manner, the optical inspection can be performed while considering the variation in gradation values for sampling areas, which is derived from the film thickness variation of the thin films between lots, in a lot, and in a wafer surface, thereby reducing detection errors due to variation in gradation values for sampling areas.

Further, the film thickness is measured at the time of wafer alignment, thereby separating the optical inspection from the film thickness measurement and suppressing increase in inspection time.

BRIEF DESCRIPTION OF THE DRAWINGS

In the accompanying drawings:

FIGS. 1A to 1D are diagrams illustrating an embodiment of measurement using an automatic optical inspection apparatus according to the present invention, in which:

FIG. 1A is an example of a plan view of a measurement chip according to the present invention;

FIG. 1B is an example of a sectional view taken along the line X-X' of the measurement chip of FIG. 1A;

FIG. 1C is an example of a plan view of a measurement wafer according to the present invention; and FIG. 1D is an example of a graph showing a relation between a film thickness and an inspection threshold value according to the present invention.

DETAILED DESCRIPTION OF THE PREFERRED EMBODIMENT

Hereinafter, an embodiment of the present invention will be described with reference to FIGS. 1A, 1B, 1C, 1D, and 2.

Figure 1A:
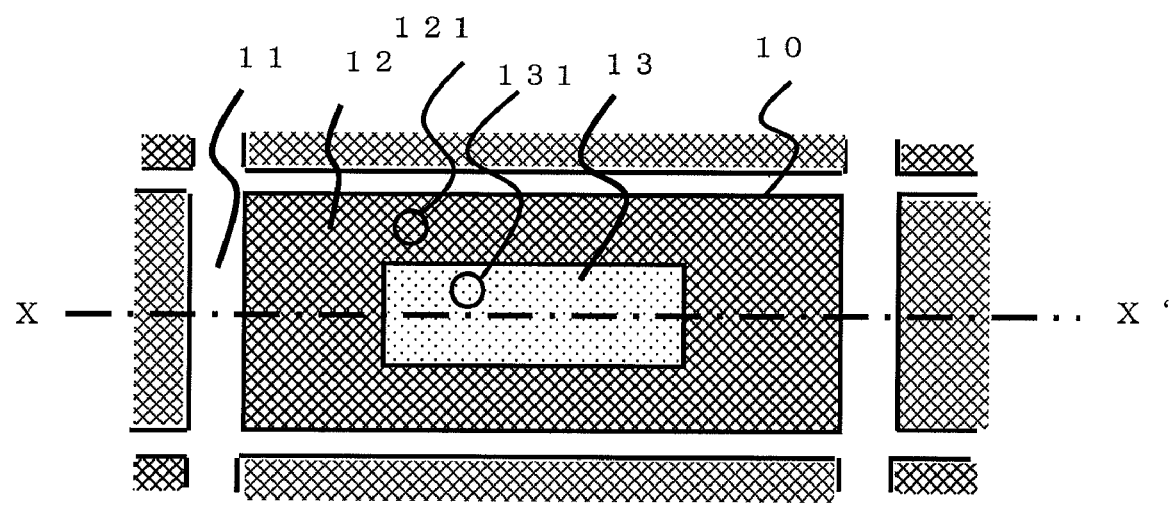
Figure 1B:
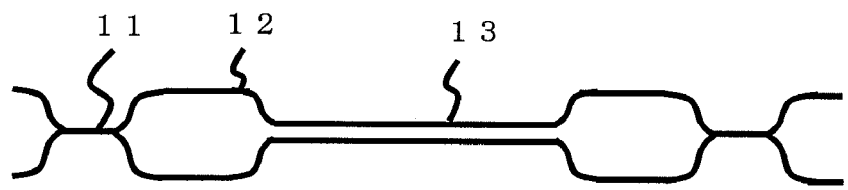
Figure 1C:
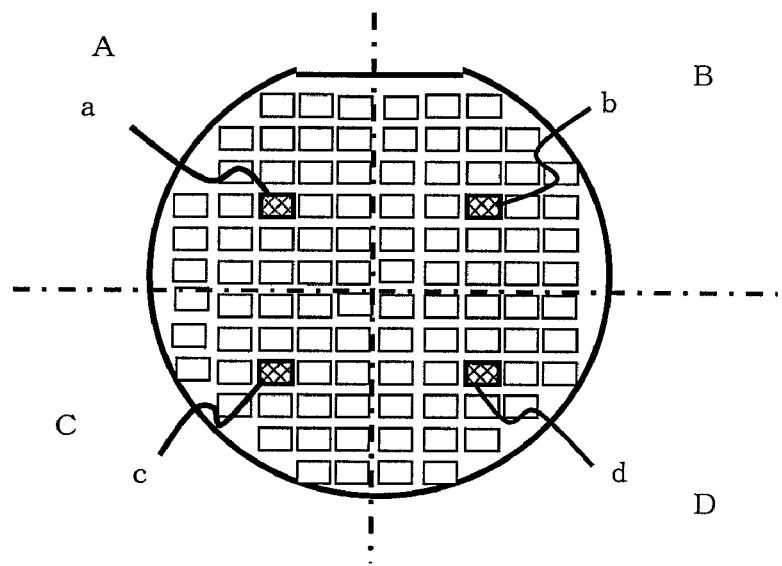

In an area of a chip 10 surrounded by a scribe line 11, a film thickness measurement point 121 of a first oxide film area 12 and a film thickness measurement point 131 of a second oxide film area 13 constituting the chip 10 with the first oxide film area 12 are set. Note that FIG. 1B illustrates a schematic sectional view taken along the line X-X' of the chip of FIG. 1A.

A wafer is divided into arbitrary areas each including chips. For example, in FIG. 1C, a wafer is divided into areas "A", "B", "C", and "D".

Subsequently, for each of the areas, at least one chip is selected to measure film thickness thereof. For example, in FIG. 1C, a chip "a" is selected for the area "A", a chip "b" for the area "B", a chip "c" for the area "C", and a chip "d" for the area "D".

Figure 1D:
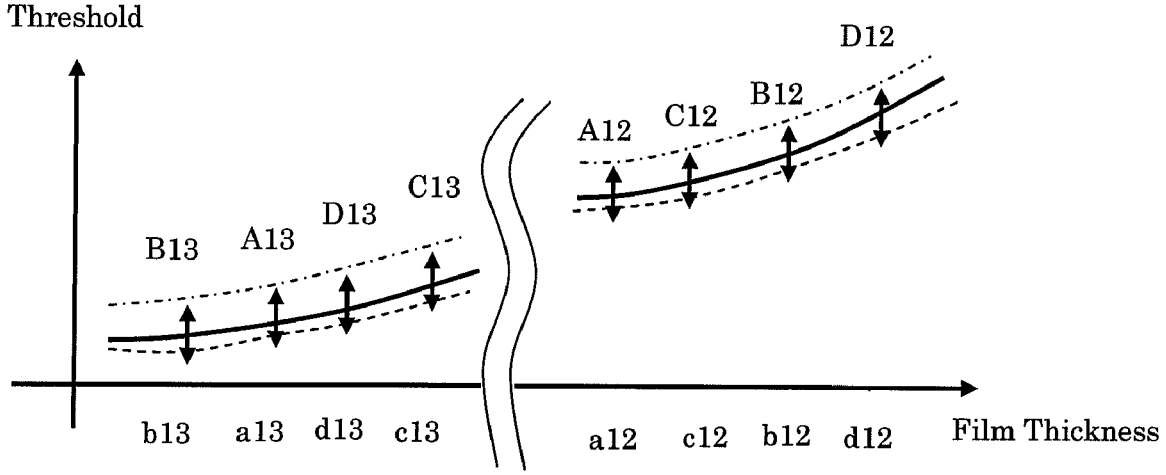

In order to define a reference sample for comparing patterns of chips, a sensitivity curve between a gradation value for a sample area and each of the film thickness measurement point 121 and the film thickness measurement point 131 is obtained using a statistical technique (for example, a least squares method). Then, with variation taken into calculation, the upper limit line and the lower limit line for inspection threshold values in film thickness of each point are set. Specifically, film thicknesses a12, a13, b12, b13, c12, c13, d12, and d13 at the film thickness measurement point 121 and the film thickness measurement point 131 of the oxide film are measured for the chips "a", "b", "c", and "d" of a wafer to be inspected, respectively. As illustrated in FIG. 1D, inspection threshold values A12, A13, B12, B13, C12, C13, D12, and D13, which correspond to their respective film thicknesses, are calculated.

The inspection of all chips belonging to the area "A" is performed using the inspection threshold values A12 and A13, the inspection of all chips belonging to the area "B" is performed using the inspection threshold values B12 and B13, the inspection of all chips belonging to the area "C" is performed using the inspection threshold values C12 and C13, and the inspection of all chips belonging to the area "D" is performed using the inspection threshold values D12 and D13.

In the above embodiment, an example of the silicon oxide film ($SiO_2$) on a silicon substrate is described, but it is possible to perform an inspection for various thin films such as a silicon nitride film ($Si_3N_4$) on one of a silicon substrate and a silicon oxide film and a polysilicon film on a silicon oxide film.

Figure 2:
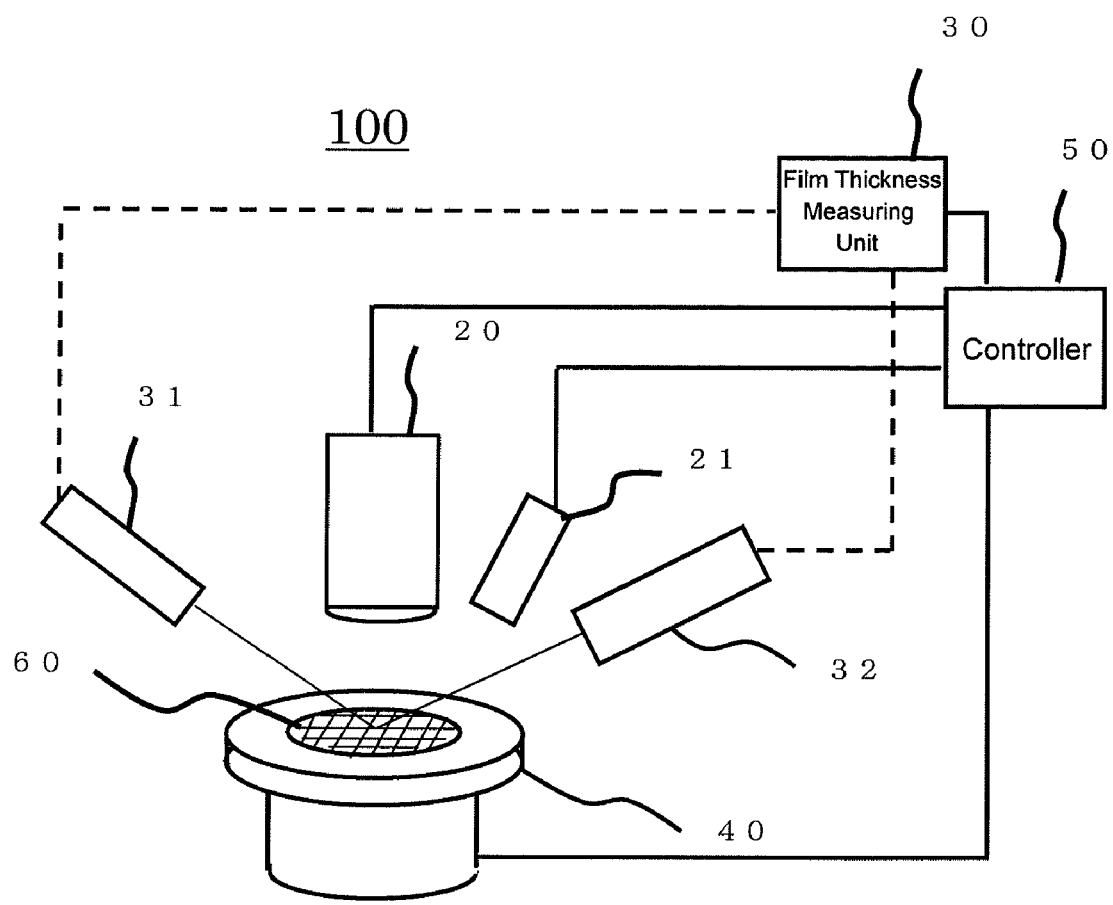
FIG. 2 is an example showing a construction of an optical inspection apparatus and a film thickness measuring device according to the present invention.

Next, the optical inspection system 100 according to the present invention comprises an optical inspection apparatus and a film thickness measuring device. With reference to FIG. 2, the positional relation between the optical inspection apparatus and the film thickness measuring device, and operation thereof will be described. The optical inspection apparatus comprises an image capturing unit 20, a lighting unit 21 and a controller 50. Since the image capturing unit 20 of the optical inspection apparatus is disposed at a position opposite to a measurement wafer 60, it is desirable that the film thickness measuring device such as an ellipsometer can perform measurement from oblique direction to the wafer.

The film thickness measuring device comprises a film thickness measuring unit 30, a measurement light emitter 31 and a reflected light receptor 32. For example, an ellipsometer may be used as the film thickness measuring device suitable for realizing the present invention since the measurement light emitter 31 and the reflected light receptor 32 are disposed in oblique direction to the measurement wafer 60, which gives no effect to the positions of the image capturing unit 20 and the lightning unit 21.

Further, the ellipsometer is suitable for measuring a specific portion of a chip, and a film thickness measuring pattern provided on a scribe line since a measuring spot (beam spot) size can be reduced to about 35 micron in diameter.

What is claimed is:

1. An optical inspection method for checking acceptability of circuits formed on the semiconductor wafer, comprising:
    measuring thicknesses of a film disposed on the semiconductor wafer at a plurality of locations on the semiconductor wafer;
    measuring levels of gradation at the plurality of locations on the semiconductor wafer;
    calculating a sensitivity curve representative of a relation between the measured levels of gradation and the measured thicknesses;
    determining acceptable ranges of gradation at one or more points in a representative circuit, from the sensitivity curve read at film thicknesses measured at the one or more points, wherein at least one representative circuit is selected from each of one or more areas defined over the semiconductor wafer; and
    determining whether levels of gradation measured in a respective circuit in each area fall within the acceptable ranges of gradation determined from the at least one representative circuit located in the corresponding area in order to determine the acceptability of the respective circuit.

2. The method according to claim 1, wherein the film is a silicon oxide film formed on a silicon substrate.

3. The method according to claim 1, wherein the film is a silicon nitride film formed on a silicon substrate or a silicon oxide film.

4. The method according to claim 1, wherein the film is a polycrystalline silicon film formed on a silicon oxide film.

5. The method according to claim 1, wherein measuring thicknesses of a film uses an ellipsometer.

6. The method according to claim 1, wherein measuring thicknesses of a film is performed at a time of wafer alignment.

* * * * *